(12) United States Patent
Pak

(10) Patent No.: US 7,714,152 B2
(45) Date of Patent: May 11, 2010

(54) CARRIER FOR OLEFIN OXIDE CATALYST

(75) Inventor: Serguei Pak, Teaneck, NJ (US)

(73) Assignee: SD Lizenzverwertungsgesellschaft mbH & Co. KG, Munich (DE)

( * ) Notice: Subject to any disclaimer, the term of this patent is extended or adjusted under 35 U.S.C. 154(b) by 17 days.

(21) Appl. No.: 11/847,422

(22) Filed: Aug. 30, 2007

(65) Prior Publication Data

US 2009/0062556 A1    Mar. 5, 2009

(51) Int. Cl.
*C07D 301/10*    (2006.01)
(52) U.S. Cl. .................. 549/536; 423/628; 502/348; 549/534
(58) Field of Classification Search ........... 549/536, 549/535, 534; 502/263, 348, 355, 243, 216, 502/221, 224, 317, 330, 347, 305, 219; 423/328.1, 423/332, 335, 345, 460, 608, 625, 635, 700, 423/628
See application file for complete search history.

(56) References Cited

U.S. PATENT DOCUMENTS

| | | | |
|---|---|---|---|
| 4,226,782 A | 10/1980 | Hayden et al. | |
| 4,242,235 A | 12/1980 | Cognion et al. | |
| 5,380,697 A | 1/1995 | Matusz et al. | |
| 5,597,773 A | 1/1997 | Evans et al. | |
| 5,929,259 A | 7/1999 | Lockemeyer | |
| 6,831,037 B2 | 12/2004 | Szymanski et al. | |
| 2004/0110973 A1 | 6/2004 | Matusz | |
| 2005/0096219 A1 | 5/2005 | Symanski et al. | |
| 2007/0184973 A1 | 8/2007 | Lockemeyer et al. | |

*Primary Examiner*—Bernard Dentz
*Assistant Examiner*—David E Gallis
(74) *Attorney, Agent, or Firm*—Scully, Scott, Murphy & Presser, P.C.

(57) ABSTRACT

A carrier for a catalyst useful for the epoxidation of an olefin which comprises an inert, refractory solid carrier is provided. The carrier has no or little absolute volume from small pores, of less than 1 micrometer, and large pores, of above 5 micrometer. By "no or little absolute volume from small pores of less than 1 micron" it is meant that the pore volume of such pores is less than 0.20 ml/g. By "no or little absolute volume from large pores of above 5 micron" it is meant that the pore volume of such pores is less than 0.20 ml/g. The invention further provides a catalyst useful for the epoxidation of an olefin supported on such a carrier and a process for the oxidation of an olefin, especially ethylene, to an olefin oxide, especially ethylene oxide.

18 Claims, No Drawings

US 7,714,152 B2

CARRIER FOR OLEFIN OXIDE CATALYST

FIELD OF THE INVENTION

The present invention relates to a carrier for a catalyst useful for the epoxidation of an olefin. More particularly, the present invention provides a carrier that has a particular pore distribution and to an epoxidation catalyst that includes the inventive carrier.

BACKGROUND OF THE INVENTION

In olefin epoxidation, an olefin is reacted with oxygen to form an olefin epoxide using a catalyst comprising a silver component, usually with one or more elements (i.e., promoters) deposited on a carrier. Catalyst performance is characterized on the basis of selectivity, activity and stability. The selectivity is the molar fraction of the converted olefin yielding the desired olefin oxide. The fraction of olefin reacted normally decreases with time and to maintain a constant product level the temperature of the reaction is increased. However this adversely affects the selectivity of the conversion to the desired product. Thus, the longer the selectivity can be maintained at a high level and at an acceptably low temperature, the longer the catalyst charge can be kept in the reactor and the more product is obtained. Quite modest improvements in selectivity and the maintenance of selectivity over longer time yield huge dividends in terms of process efficiency.

Beside the chemical composition of a supported silver-based epoxidation catalyst, the physical characteristics of the finished catalyst as well the support have been an integral part of catalyst development. Generally, the silver-based catalyst support shows a characteristic pore volume and pore size distribution. Furthermore, the surface area and the water absorption are well-known characteristics for such catalyst supports. It has now been found that the physical characteristics of the finished catalyst and the impact of these characteristics on the catalyst performance are more complicated than heretofore believed, especially if the catalyst is promoted with rhenium. In addition to the surface area, the pore volume and the pore size distribution, the pattern of the pore size distribution, especially the number and the specific characteristics of different modes, has been found to have a significant positive impact on the catalyst selectivity.

A number of patents describe preparation and selection of different, preferential carriers for ethylene epoxidation catalysts. For example, U.S. Pat. No. 4,242,235 discloses low surface area, less than 10 m$^2$/g, carriers. This prior art carrier has a porosity of 60% and is bimodal with mean pore diameters in the range of 1-5 micron and 60-200 microns. Each of the ranges disclosed in the '235 patent represents at least 35% and at most 65% of the total porosity.

U.S. Pat. No. 4,226,782 describes a carrier having a surface area in the range from 0.05 to 10 m$^2$/g, a porosity from 30-80%, and pores of 0.1 to 20 microns. U.S. Pat. No. 5,266,548 describes a method of making alpha-alumina from 95% high purity alumina. Preferably, the carrier disclosed in the '548 patent has a porosity of from 0.2 ml/g to 0.6 ml/g, and a surface area from 0.2 m$^2$/g to 10 m$^2$/g. Additionally, the '548 patent discloses that the average pore size of the carrier is from 0.1 microns to 100 microns, preferably in the range from 0.1-10 micron, and more preferably from 0.2-5 micron.

U.S. Pat. No. 5,380,697 describes the preparation of an alumina carrier from alpha-alumina particles having a median grain size of from 0.4 micron to 4 micron and a sol-gel. The carriers made in the '697 patent typically have a pore volume (i.e., water absorption) ranging from about 0.2 cc/g to about 0.6 cc/g, preferably from about 0.3 cc/g to about 0.5 cc/g and a surface area ranging from about 0.15 m$^2$/g to about 3 m$^2$/g, preferably from about 0.3 m$^2$/g to about 2 m$^2$/g.

U.S. Pat. No. 5,597,773 discloses a large number of refractory carriers, with carriers made of alpha-alumina being highly preferred. In the '773 patent, preference is given to the use of alpha-alumina carriers having a specific surface area, as measured by a BET method, of from about 0.03 m$^2$/g to about 10 m$^2$/g, preferably from about 0.05 m$^2$/g to about 5 m$^2$/g, more preferably from about 0.1 m$^2$/g to about 3 m$^2$/g, and a water pore volume, as measured by conventional water absorption techniques, from about 0.1 cc/g to about 0.75 cc/g by volume, preferably from about 0.3 cc/g to about 0.5 cc/g.

In U.S. Pat. No. 5,929,259, a carrier for ethylene oxide catalysts having a porosity at least 50% and more desirably from about 60% to about 75% is disclosed. The surface area of the carrier disclosed in the '259 patent is preferably in the range 0.4-5 m$^2$/g, and more preferably 0.6-1.2 m$^2$/g.

U.S. Pat. No. 6,831,037 describes a technique for the preparation of an alumina carrier. The carrier is 95% alpha-alumina having a surface area in the range from 1.0-2.6 m$^2$/g, and a water absorption from 35-55%. This prior art carrier is advantageous for ethylene oxide catalyst preparation when at least 70% of pore volume is in the range from 0.2-10 microns, which provide at least 0.27 ml/g of total pore volume. Pores with diameters less than 0.2 micron provide 0-10% of pore volume, and pores with diameters more than 10 micron provide less than 20% of total pore volume.

U.S. Patent Application Publication No. 2004/0110973 A1 discloses a method for the preparation of an alumina carrier from two alpha-alumina particulates. This prior art carrier has 75% of pores with a diameter in the range from 0.2-10 micron, less than 20% of pores with diameter of more than 10 microns, and less than 10% of pores with diameter of less than 0.2 micron. Water absorption of this prior art carrier is at least 0.35 ml/g, and the surface area is in the range from 0.6-5 m$^2$/g.

U.S. Patent Application Publication No. 2005/0096219 A1 found advantages to provide a carrier which has a minimum of very large pores, greater than 10 micron, and water absorption of 35 to 55% and a surface area of at least 1.0 m$^2$/g. A method of making such a carrier is also described in the '219 publication.

As described above a catalyst for ethylene epoxidation requires a carrier with specific physical properties. It would be desirable to improve the catalytic selectivity, activity and stability of the catalysts by improving carrier characteristics. It has been unexpectedly found by the applicants of the present application that the pore distribution of the carrier, and particularly the absolute value of pore volume from the pores of a different diameter range, define performance of an ethylene oxide catalyst, particularly selectivity and stability.

SUMMARY OF THE INVENTION

The present invention provides a carrier for a catalyst useful for the epoxidation of an olefin which comprises a refractory solid carrier. The inventive carrier has no or little absolute volume from small pores, of less than 1 micrometer, and large pores, of above 5 micrometer. By "no or little absolute volume from small pores of less than 1 micron" it is meant that the pore volume of such pores is less than 0.20 ml/g. By "no or little absolute volume from large pores of above 5 micron" it is meant that the pore volume of such pores is less than 0.20 ml/g.

In general terms, the inventive carrier has a pore volume from pores with less than 1 micron in diameter of less than 0.201/g and a pore volume from pores with greater than 5 micron in diameter of less than 0.20 ml/g. In particular, the inventive carrier has a total pore volume from 0.2 ml/g to 0.6 ml/g, a surface area from about 0.3 to about 3.0 m$^2$/g, at least 40% of pore volume from pores with diameters between 1 and 5 micrometers, and a median pore diameter between 1 and 5 micrometers, and wherein the pore volume from pores with a diameter of greater than 5 micrometers is less than 0.20 ml/g and the pore volume from pores with a diameter of less than 1 micrometer is less than 0.20 ml/g.

The invention further provides a catalyst useful for the epoxidation of an olefin supported on such a carrier. In addition to the inventive carrier, the catalyst of the present invention further includes a catalytic effective amount of silver and a promoting effective amount of one or more promoters. Typical promoters include, but are not limited to an alkali metal, and a transition metal, especially rhenium.

The invention even further provides a process for the oxidation of an olefin, especially ethylene, to an olefin oxide, especially ethylene oxide, which comprises the vapor phase oxidation of an olefin with molecular oxygen in a fixed bed, tubular reactor, in the presence of the above supported catalyst.

DETAILED DESCRIPTION OF THE INVENTION

As stated above, the present invention provides a carrier for a silver-based epoxidation catalyst that has no or little pore volume from the pores with less than 1 micron in diameter and larger than 5 micron in diameter. The present invention also provides a silver-based epoxidation catalyst including the inventive carrier. The present invention also describes a method of oxidizing an olefin, particularly ethylene, to an olefin oxide, particular ethylene oxide.

The carrier employed in this invention may be prepared or selected from a large number of solid, refractory carriers commercially available. The inventive carrier is relatively inert to the epoxidation feedstock materials, products and reaction conditions for the intended use, such as for the epoxidation of an olefin, for example the oxidation of ethylene to ethylene oxide by the vapor phase oxidation of ethylene with molecular oxygen. The carrier may comprise aluminum oxide such as alpha-alumina, charcoal, pumice, magnesia, zirconia, titania, kieselguhr, fuller's earth, silicon carbide, silica, silicon carbide, silicon dioxide, clays, artificial zeolites, natural zeolites, ceramics and combination thereof. The preferred carriers are alpha-alumina particles which are often bonded together by a bonding agent and have a very high purity, i.e., about 95% or more, preferably 98 wt. % or more alpha-alumina. Remaining components may be other phases of alumina, silica, alkali metal oxides (e.g., sodium oxide) and trace amounts of other metal-containing and/or non-metal-containing additives or impurities. A wide variety of such carriers are commercially available. Suitable alumina carriers are manufactured and generally commercially available from United Catalysts, Inc., of Louisville, Ky., and the Norton Company, of Akron, Ohio.

Certain types of alpha alumina-containing carriers are particularly preferred. These alpha alumina carriers are characterized by having a B.E.T. surface area from about 0.3 m$^2$/g to about 3 m$^2$/g, preferably from about 0.6 m$^2$/g to about 2.5 m$^2$/g, more preferably from about 0.9 m$^2$/g to about 2.0 m$^2$/g; and a water pore volume from about 0.10 m$^2$/g to about 0.80 cc/g, preferably from about 0.20 cc/g to about 0.60 cc/g. In a preferred carrier, at least 40% of the pore volume comes from pores with diameters between 1 and 5 micrometers; preferably at least 60%; and most preferably at least 80%. The median pore distribution is between 1 and 5 micrometers; preferably between 1 and 4.5 micrometers; and most preferably between 1 and 4 micrometers. The pore volume from pores with a diameter of greater than 5 micrometers is less than 0.20 ml/g; preferably less than 0.10 ml/g; and most preferably less than 0.05 ml/g. The pore volume from pores with a diameter of less than 1 micrometer is less than 0.20 ml/g; preferably less than 0.16 ml/g; and most preferably less than 0.12 ml/g.

In one preferred embodiment of the present invention, the carrier has a total pore volume from about 0.2 to 0.6 ml/g.

Regardless of the character of the carrier used, it is usually shaped into particles, chunks, pieces, pellets, rings, spheres, wagon wheels, cross-partitioned hollow cylinders, and the like, of a size suitable for employment in fixed bed reactors. Desirably, the carrier particles may have "equivalent diameters" in the range from about 3 mm to about 10 mm and preferably in the range from about 4 mm to about 8 mm, which are usually compatible with the internal diameter of the tube reactors in which the catalyst is placed. "Equivalent diameter" is the diameter of a sphere having the same external surface (i.e. neglecting surface within the pores of the particle) to volume ratio as the carrier particles being employed.

In general, a suitable catalyst carrier of the present invention can be prepared by mixing the refractory material, such as alumina, a solvent such as water, a temporary binder or burnout material, a permanent binder and/or a porosity controlling agent. Temporary binders, or burnout materials, include cellulose, substituted celluloses, e.g., methylcellulose, ethylcellulose, and carboxyethylcellulose, stearates, such as organic stearate esters, e.g., methyl or ethyl stearate, waxes, granulated polyolefins, particularly polyethylene and polypropylene, walnut shell flour, and the like which are decomposable at the temperatures employed. These are responsible for producing the porosity of the carrier material. Burnout material is used primarily to ensure the preservation of a porous structure during the green, or unfired phase in which the mixture may be shaped into particles by molding or extrusion processes. It is essentially totally removed during the firing to produce the finished carrier. The carriers of the invention are preferably made with the inclusion of a bond material such as silica with an alkali metal compound in a sufficient amount to substantially prevent the formation of crystalline silica compounds. Permanent binders, include inorganic clay-type materials. A convenient binder material which may be incorporated with the alumina particles is a mixture of boehmite, an ammonia stabilized silica sol and a soluble sodium salt. The formed paste is extruded or molded into the desired shape and fired at a temperature from about 1200° C. to about 1600° C. to form the carrier. Where the particles are formed by extrusion it may be desirable to include conventional extrusion aids. The amounts of the components to be used are to some extent interdependent and will depend on a number of factors that relate to the equipment used. However these matters are well within the general knowledge of a person skilled in the art of extruding ceramic materials.

The performance of the carrier is enhanced if it is treated by soaking the carrier in a solution of an alkali hydroxide such as sodium hydroxide, potassium hydroxide, or an acid such as HNO$_3$ as described in U.S. Patent Application Publication No. 2006/0252643 A1. After treatment, the carrier is preferably washed, such as with water, to remove unreacted dissolved material and treating solution and optionally dried.

In order to produce a catalyst for the oxidation of an olefin to an olefin oxide, a carrier having the above characteristics is then provided with a catalytically effective amount of silver thereon. The catalyst is prepared by impregnating the inventive carrier with silver ions, compounds, complexes and/or salts dissolved in a suitable solvent sufficient to cause deposition of silver precursor compound onto the carrier. The impregnated carrier is then removed from the solution and the deposited silver compound is reduced to metallic silver by high temperature calcination. Also preferably deposited on the carrier either prior to, coincidentally with, or subsequent to the deposition of the silver are suitable promoters in the form of ions, compounds and/or salts of an alkali metal dissolved in a suitable solvent. Also deposited on the carrier either prior to, coincidentally with, or subsequent to the deposition of the silver and/or alkali metal are suitable transition metal ions, compounds, complexes and/or salts dissolved in an appropriate solvent.

The original or treated carrier as described above is impregnated with a silver impregnating solution, preferably an aqueous silver solution. The carrier is also impregnated at the same time or in a separate step with various catalyst promoters. Preferred catalysts prepared in accordance with this invention contain up to about 45% by weight of silver, expressed as metal, deposited upon the surface and throughout the pores of a porous refractory carrier. Silver contents, expressed as metal, from about 1 to about 40% based on weight of total catalyst are preferred, while silver contents from about 8 to about 35% are more preferred. The amount of silver deposited on the support or present on the carrier is that amount which is a catalytically effective amount of silver, i.e., an amount which economically catalyzes the reaction of ethylene and oxygen to produce ethylene oxide. As used herein, the term "catalytically effective amount of silver" refers to an amount of silver that provides a measurable conversion of ethylene and oxygen to ethylene oxide and selectivity and activity stability within catalyst life. Useful silver containing compounds non-exclusively include silver oxalate, silver nitrate, silver oxide, silver carbonate, a silver carboxylate, silver citrate, silver phthalate, silver lactate, silver propionate, silver butyrate and higher fatty acid salts and combinations thereof.

The catalyst comprises a catalytically effective amount of silver, a promoting amount of alkali metal, a promoting amount of a transition metal supported on the inventive carrier. As used herein the term "promoting amount" of a certain component of a catalyst refers to an amount of that component that works effectively to provide an improvement in one or more of the catalytic properties of that catalyst when compared to a catalyst not containing said component. The exact concentrations employed, of course, will depend upon, among other factors, the desired silver content, the nature of the carrier, the viscosity of the liquid, and solubility of the silver compound.

In addition to silver, the catalyst also contains an alkali metal promoter selected from lithium, sodium, potassium, rubidium, cesium or combinations thereof, with, cesium being preferred. The amount of alkali metal deposited on the carrier or catalyst or present on the carrier or catalyst is to be a promoting amount. Preferably the amount will range from about 10 ppm to about 3000 ppm, more preferably from about 15 ppm to about 2000 ppm and even more preferably from about 20 ppm to about 1500 ppm and yet even more preferably from about 50 ppm to about 1000 ppm by weight of the total catalyst, measured as the metal.

The catalyst also preferably contains a transition metal promoter which comprises an element from Groups 5b, 6b, 7b and 8 of the Periodic Table of the Elements, and combinations thereof. Preferably the transition metal comprises an element selected from Group 7b of the Periodic Table of the Elements. More preferred transition metals are rhenium, molybdenum, and tungsten, with molybdenum and rhenium most preferred. The amount of transition metal promoter deposited on the carrier or catalyst or present on the carrier or catalyst is to be a promoting amount. The transition metal promoter may be present in an amount from about 0.1 micromoles per gram to about 10 micromoles per gram, preferably from about 0.2 micromoles per gram to about 5 micromoles per gram, and more preferably from about 0.5 micromoles per gram to about 4 micromoles per gram of total catalyst, expressed as the metal. The catalyst may further comprise a promoting amount of one or more sulfur components, one or more fluorine containing components, or combinations thereof.

The silver solution used to impregnate the carrier may also comprise an optional solvent or complexing/solubilizing agent such as is known in the art. A wide variety of solvents or complexing/solubilizing agents may be employed to solubilize silver to the desired concentration in the impregnating medium. Useful complexing/solubilizing agents include amines, ammonia, lactic acid and combinations thereof. Amines include an alkylene diamine having from 1 to 5 carbon atoms. In one preferred embodiment, the solution comprises an aqueous solution of silver oxalate and ethylene diamine. The complexing/solubilizing agent may be present in the impregnating solution in an amount from about 0.1 to about 5.0 moles of ethylene diamine per mole of silver, preferably from about 0.2 to about 4.0 moles, and more preferably from about 0.3 to about 3.0 moles of ethylene diamine for each mole of silver.

When a solvent is used it may be water-based, or organic-based, and may be polar or substantially or totally non-polar. In general, the solvent should have sufficient solvating power to solubilize the solution components. At the same time, it is preferred that the solvent be chosen to avoid having an undue influence on or interaction with the solvated promoters. Examples of organic-based solvents include, but are not limited to, alcohols, in particular alkanols; glycols, in particular alkyl glycols; ketones; aldehydes; amines; tetrahydrofuran; nitrobenzene; nitrotoluene and the like. Organic-based solvents which have 1 to about 8 carbon atoms per molecule are preferred. Mixtures of organic solvents or of water and one or more organic solvents may be used, provided that such mixed solvents function as desired herein.

The concentration of silver salt in the solution is in the range from about 0.1% by weight to the maximum permitted by the solubility of the particular salt/solubilizing agent combination employed. It is generally very suitable to employ silver salt solutions containing from about 0.5% to about 45% by weight of silver with silver salt concentrations from about 5 to about 30% by weight being preferred.

Impregnation of the selected carrier is achieved in conventional manners by excess solution impregnation, incipient wetness, etc. Typically carrier material is placed in the silver solution until a sufficient amount of the solution is absorbed by the carrier. Preferably the quantity of the silver solution used to impregnate the porous carrier is no more than is necessary to fill the pore volume of the carrier. The silver containing liquid penetrates by absorption, capillary action and/or vacuum into the pores of the carrier. A single impregnation or a series of impregnations, with or without intermediate drying, may be used, depending in part on the concentration of the silver salt in the solution. Impregnation procedures are described in U.S. Pat. Nos. 4,761,394, 4,766, 105m, 4,908,343, 5,057,481, 5,187,140, 5,102,848, 5,011, 807, 5,099,041 and 5,407,888, which are incorporated herein by reference. Known prior procedures of pre-deposition, co-deposition and post-deposition of various the promoters can be employed.

Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may be operated at a different set of conditions wherein the improvement shows up in the activity rather than the selectivity and an operator of an ethylene oxide plant will intentionally change the operating conditions in order to take advantage of certain catalytic properties even at the expense of other catalytic properties in order to optimize conditions and results by taking into account feedstock costs, energy costs, by-product removal costs and the like. The particular combination of silver, carrier, alkali metal promoter, and transition metal promoter of the instant invention will provide an improvement in one or more catalytic properties over the same combination of silver and carrier and none, or only one promoter.

After impregnation, the carrier impregnated with silver precursor compound and the promoters is calcined or activated, for a time sufficient to reduce the silver component to metallic silver and to remove volatile decomposition products from the silver containing support. The calcination is accomplished by heating the impregnated carrier, preferably at a gradual rate, to a temperature in the range from about 200° C. to about 600° C., preferably from about 250° C. to about 500° C., and more preferably from about 300° C. to about 450° C., at a reaction pressure in the range from 0.5 to 35 bar, for a time sufficient to convert the contained silver to silver metal and to decompose all or substantially all of present organic materials and remove the same as volatiles. In general, the higher the temperature, the shorter the required reduction period. A wide range of heating periods has been suggested in the art to thermally treat the impregnated support. U.S. Pat. No. 3,563,914 suggests heating for less than 300 seconds, while U.S. Pat. No. 3,702,259 discloses heating from 2 to 8 hours at a temperature of from 100° C. to 375° C. to reduce the silver salt in the catalyst; usually for from about 0.5 to about 8 hours. In the invention, it is however only important that the reduction time be correlated with temperature such that substantially complete reduction of silver salt to catalytically active metal is accomplished. A continuous or step-wise heating program may be used for this purpose.

Olefin Oxide Production

Generally, the commercially practiced olefin oxide production processes are carried out by continuously contacting an oxygen containing gas with an olefin, especially ethylene, in the presence of the catalyst at a temperature in the range from about 180° C. to about 330° C. and preferably about 200° C. to about 325° C., more preferably from about 225° C. to about 270° C., at a pressure which may vary from about atmospheric pressure to about 30 atmospheres depending on the mass velocity and productivity desired. Pressures in the range from about atmospheric to about 500 psi are generally employed. Higher pressures may, however, be employed within the scope of the invention. Residence times in large-scale reactors are generally on the order of about 0.1-5 seconds. Oxygen may be supplied to the reaction in an oxygen containing stream, such as air or as commercial oxygen. The resulting olefin oxide, e.g., ethylene oxide, is separated and recovered from the reaction products using conventional methods. However, for this invention, the olefin oxide process envisions the normal gas recycle encompassing carbon dioxide recycle in the normal concentrations, e.g., about 0.5 to 6 volume percent. A usual process for the oxidation of ethylene to ethylene oxide comprises the vapor phase oxidation of ethylene with molecular oxygen in the presence of the inventive catalyst in a fixed bed, tubular reactor. Conventional commercial fixed bed ethylene oxide reactors are typically in the form of a plurality of parallel elongated tubes (in a suitable shell) approximately 0.7 to 2.7 inches O.D. and 0.5 to 2.5 inches I.D. and 15-45 feet long filled with catalyst.

The inventive catalysts have been shown to be particularly selective catalysts in the oxidation of ethylene with molecular oxygen to ethylene oxide. The conditions for carrying out such an oxidation reaction in the presence of the catalyst of the present invention broadly comprise those described in the prior art. This applies, for example, to suitable temperatures, pressures, residence times, diluent materials such as nitrogen, carbon dioxide, steam, argon, methane or other saturated hydrocarbons, the presence or absence of moderating agents to control the catalytic action, for example, 1,2-dichloroethane, vinyl chloride or chlorinated polyphenyl compounds, the desirability of employing recycle operations or applying successive conversion in different reactors to increase the yields of ethylene oxide, and any other special conditions which may be selected in processes for preparing ethylene oxide. Molecular oxygen employed as a reactant may be obtained from conventional sources. The suitable oxygen charge may be relatively pure oxygen, a concentrated oxygen stream comprising oxygen in major amount with lesser amounts of one or more diluents such as nitrogen, argon, etc., or another oxygen containing stream such as air. The use of the present catalysts in ethylene oxidation reactions is in no way limited to the use of specific conditions among those which are known to be effective.

The resulting ethylene oxide is separated and recovered from the reaction products by conventional methods known and used in the art. Use of the silver catalysts of the invention in ethylene oxide production processes gives higher overall ethylene oxidation selectivities to ethylene oxide at a given ethylene conversion than are possible with conventional catalysts.

In the production of ethylene oxide, reactant feed mixtures may contain 0.5 to 45% ethylene and 3 to 15% oxygen, with the balance comprising comparatively inert materials including such substances as nitrogen, carbon dioxide, methane, ethane, argon and the like. In a preferred application of the silver catalysts of the invention, ethylene oxide is produced when an oxygen containing gas of about 95% or more of oxygen is used. Only a portion of the ethylene usually is reacted per pass over the catalyst and after separation of the desired ethylene oxide product and the removal of appropriate purge stream and carbon dioxide to prevent uncontrolled build up of inerts and/or by-products, unreacted materials are returned to the oxidation reactor. For purposes of illustration only, the following are conditions that are often used in current commercial ethylene oxide reactor units. GHSV—1500-10,000; Inlet pressure—150-400 psig; Inlet Feed: ethylene—1-40%; $O_2$—3-12%; $CO_2$—2-40%; ethane 0-3%; argon and/or methane and/or nitrogen: 0.3-20 ppmv total diluent chlorohydrocarbon moderator; coolant temperature—180-315° C.; $O_2$ conversion level—10-60%; EO Production (Work Rate) 2-16 lbs. EO/cu.ft. catalyst/hr.

In other descriptions of processes of ethylene oxide production addition of oxygen-containing gases to the feed increased the efficiency. For example in U.S. Pat. No. 5,112, 795 5 ppm of nitric oxide was added to the gas feed of composition: 8 volume % oxygen, 30 volume % ethylene, about 5 ppmw ethyl chloride and the balance nitrogen.

The following non-limiting examples are provided to illustrate some embodiments of the present invention and to demonstrate some advantages of utilizing the inventive carrier in the epoxidation of ethyelene to ethylene oxide. The following were used in the examples of the present application:

Catalysts Preparation and Testing.

a. Silver Stock Solution Preparation.

A silver solution was prepared using the following components (parts are by weight):

Silver oxide—834 parts
Oxalic acid—444 parts
Ethylene diamine—509 parts

Silver oxide was mixed with water, at room temperature, followed by the gradual addition of the oxalic acid. The mixture was stirred for 15 minutes and at that point, the color of the black suspension of silver oxide changed to the gray/brown color of silver oxalate. The mixture was filtered and the solids were washed with 3 liters of de-ionized water. The sample was placed in an ice bath and stirred while ethylene diamine and water (as a 66/34 mixture) were added slowly in order to maintain the reaction temperature lower than 33° C. After the addition of the ethylene diamine/water mixture, the solution was filtered at room temperature. The clear filtrate was utilized as a silver/amine stock solution for catalyst preparation.

b. Promoter Addition:

Promoters were added in catalytically active amounts individually or as a mixture of water based solutions: for example, Cs as CsOH, Li as $LiNO_3$, Re as $HReO_4$, W as ammonium metatungstate, and S as $(NH_4)_2SO_4$. Promoter concentrations were optimized to provide maximum stability at high selectivity. Specifically, promoter concentrations were within the broad ranges mentioned above and are also within the ranges found within examples 3-10 through 7-20 of U.S. Pat. No. 4,766,105.

c. Carriers.

Carriers A, B, C, D, E, F, G used in the examples are as indicated in Table I. The carriers were treated with NaOH solutions as indicated in the Table 1 at 80° C. for 1.5 hour followed by DI water rinsing of the carriers to remove NaOH.

TABLE I

Carrier properties and treatment.

| Carrier | Total Pore Volume, ml/g | Surface Area, $m^2/g$ | NaOH treatment, M |
|---|---|---|---|
| A | 0.320 | 0.89 | 0.25 |
| B | 0.417 | 0.86 | 0.25 |
| C | 0.369 | 0.93 | 0.25 |
| D | 0.398 | 1.03 | 0.025 |
| E | 0.535 | 1.15 | 0.25 |
| F | 0.360 | 1.19 | 0.025 |
| G | 0.376 | 1.24 | 0.25 | d. Carrier Impregnation:

A 100 g to 200 g of carrier sample was placed in a pressure vessel and then exposed to vacuum until the pressure was below 50 mm Hg. 200-300 ml of the adjusted silver/promoter solution was introduced to the flask while it was still under vacuum. The pressure of the vessel was allowed to rise to atmospheric pressure. The catalyst was separated from the solution and was ready for calcination.

Silver catalysts promoted with Cs, Li, Re, W and S were prepared on carriers A, B, C, D, E, F and G. The catalysts contained a catalytically effective concentration of silver between 12% and 18% as limited by total pore volume of carriers.

e. Catalyst Calcination:

Calcination was achieved by heating the catalyst up to the decomposition temperature of the silver salt. This was achieved via heating in a furnace that has several heating zones in a controlled atmosphere. The catalyst was loaded on a moving belt that entered the furnace at ambient temperature. The temperature was gradually increased as the catalyst passed from one zone to the next. It was increased, up to 400° C. in the hottest zone. After the heating zones, the belt passed through a cooling zone that gradually cooled the catalyst to near ambient temperature. The atmosphere in the furnace was controlled through the use of nitrogen flow in the heating zones.

f. Catalyst Testing:

The catalyst, 4 g, was tested in a heated stainless steel tube. A gas mixture containing 15% ethylene, 7% oxygen, and 78% inert, mainly nitrogen and carbon dioxide, was passed through the catalyst at 300 psig. The temperature of the reaction was adjusted to maintain catalyst at weight work rate (WWR)=540.

EXAMPLE 1

This example demonstrates that at comparable surface areas the smaller the pore volume from pores with a diameter under 1 micron, the higher the selectivity and the better the stability. For comparison of stability the time catalysts performed at selectivity above 85% was measured.

| Carrier/catalyst parameters | A | B | C |
|---|---|---|---|
| | Carriers | | |
| Pores 1 micron and less. Pore Volume, ml/g | 0.118 | 0.130 | 0.139 |
| | Catalysts | | |
| Selectivity, % | 89.2 | 87.5 | 87.0 |
| Stability, h | 375 | 294 | 214 |

EXAMPLE 2

This example demonstrates that at comparable pore volume from pores with diameter less than 1 micrometer, the smaller the pore volume from pores with diameter above 5 micrometers the higher the selectivity.

| Carrier/catalyst parameters | D | C | E |
|---|---|---|---|
| | Carriers | | |
| Pores 1 micron and less. Pore Volume, ml/g | 0.132 | 0.139 | 0.135 |
| Pores 5 micron and larger. Pore Volume, ml/g | 0.029 | 0.113 | 0.219 |
| | Catalysts | | |
| Selectivity, % | 88.1 | 87.0 | 86.2 |

EXAMPLE 3

This example demonstrates that when the pore volume from pores greater than 5 microns is low, less than 0.1 ml/g, the smaller the pore volume from pores with diameters below 1 micrometer the higher selectivity.

| Carrier/catalyst parameters | A | D | F | G |
|---|---|---|---|---|
| Carriers | | | | |
| Pores 1 micron and less. Pore Volume, ml/g | 0.118 | 0.132 | 0.171 | 0.176 |
| Pores 5 micron and larger. Pore Volume, ml/g | 0.041 | 0.029 | 0.028 | 0.032 |
| Catalysts | | | | |
| Selectivity, % | 89.2 | 88.1 | 87.2 | 86.3 |

While the present invention has been demonstrated and described with reference to preferred embodiments, it will be readily appreciated by those of ordinary skill in the art that various changes and modifications may be made without departing from the spirit and scope of the invention. It is therefore intended that the claims be interpreted to cover the disclosed embodiment, those alternatives which have been discussed, and any and all equivalents thereto.

What is claimed is:

1. A catalyst useful for the epoxidation of an olefin which comprises an alpha alumina carrier and a catalytically effective amount of silver thereon, said alpha alumina carrier having a pore volume from pores with less than 1 micron in diameter of less than 0.20 ml/g, a pore volume from pores with greater than 5 micron in diameter of less than 0.20 ml/g, and a pore volume from pores between 1 micron in diameter and 5 microns in diameter comprising at least 40 percent of a total pore volume.

2. The catalyst of claim 1 farther comprising a promoting amount of a promoter thereon, the promoter comprising one or more of an alkali metal containing compounds, one or more transition metal containing compounds, one or more sulfur components, one or more fluorine containing components, or combinations thereof.

3. The catalyst of claim 2 wherein the promoter is one or more transition metal containing compounds comprising an element selected from Groups 5b, 6b, 7b and 8 of the Periodic Table of the Elements, and combinations thereof.

4. The catalyst of claim 3 wherein the one or more transition metal containing compounds comprises rhenium, molybdenum, tungsten or combinations thereof.

5. The catalyst of claim 2 wherein the promoter is an alkali metal containing compound comprises lithium, sodium, potassium, rubidium, cesium or combinations thereof.

6. A catalyst useful for the epoxidation of an olefin which comprises an alpha alumina carrier and a catalytically effective amount of silver thereon, said alpha alumina carrier having a total pore volume from 0.2 ml/g to 0.6 ml/g, a surface area from about 0.3 to about 3.0 $m^2/g$, at least 40% of pore volume from pores with diameters between 1 and 5 micrometers, and a median pore diameter between 1 and 5 micrometers, and wherein the pore volume from pores with a diameter of greater than 5 micrometers is less than 0.20 ml/g and the pore volume from pores with a diameter of less than 1 micrometer is less than 0.20 ml/g.

7. The catalyst of claim 6 further comprising a promoting amount of a promoter thereon, the promoter comprising one or more of an alkali metal containing compounds, one or more transition metal containing compounds, one or more sulfur components, one or more fluorine containing components, or combinations thereof.

8. The catalyst of claim 7 wherein the promoter is one or more transition metal containing compounds comprising an element selected from Groups 5b, 6b, 7b and 8 of the Periodic Table of the Elements, and combinations thereof.

9. The catalyst of claim 8 wherein the one or more transition metal containing compounds comprises rhenium, molybdenum, tungsten or combinations thereof.

10. The catalyst of claim 7 wherein the promoter is an alkali metal containing compound comprises lithium, sodium, potassium, rubidium, cesium or combinations thereof.

11. A process for the oxidation of ethylene to ethylene oxide which comprises the vapor phase oxidation of ethylene with molecular oxygen in a fixed bed, tubular reactor, in the presence of the catalyst of claim 1.

12. A process for the oxidation of ethylene to ethylene oxide which comprises the vapor phase oxidation of ethylene with molecular oxygen in a fixed bed, tubular reactor, in the presence of the catalyst of claim 6.

13. A catalyst useful for the epoxidation of an olefin which comprises an alpha alumina carrier and a catalytically effective amount of silver thereon, said alpha alumina carrier having a pore volume from pores with less than 1 micron in diameter of less than 0.10 ml/g, a pore volume from pores with greater than 5 micron in diameter of less than 0.16 ml/g, and a pore volume from pores between 1 micron in diameter and 5 microns in diameter comprising at least 40 percent of a total pore volume.

14. A catalyst useful for the epoxidation of an olefin which comprises an alpha alumina carrier and a catalytically effective amount of silver thereon, said alpha alumina carrier having a pore volume from pores with less than 1 micron in diameter of less than 0.05 ml/g, a pore volume from pores with greater than 5 micron in diameter of less than 0.12 ml/g, and a pore volume from pores between 1 micron in diameter and 5 microns in diameter comprising at least 40 percent of a total pore volume.

15. The catalyst of claim 1 wherein said alpha alumina carrier has a water absorption from 0.60 to 0.80 cubic centimeters per gram.

16. The catalyst of claim 6 wherein said alpha alumina carrier has a water absorption from 0.60 to 0.80 cubic centimeters per gram.

17. The catalyst of claim 13 wherein said alpha alumina carrier has a water absorption from 0.60 to 0.80 cubic centimeters per gram.

18. The catalyst of claim 14 wherein said alpha alumina carrier has a water absorption from 0.60 to 0.80 cubic centimeters per gram.

* * * * *

(12) INTER PARTES REEXAMINATION CERTIFICATE (831st)
United States Patent
Pak

(10) Number: US 7,714,152 C1
(45) Certificate Issued: Feb. 26, 2014

(54) CARRIER FOR OLEFIN OXIDE CATALYST

(75) Inventor: Serguei Pak, Teaneck, NJ (US)

(73) Assignee: SD Lizenzverwertungsgesellschaft mbH & Co. KG, Munich (DE)

Reexamination Request:
No. 95/001,865, Dec. 30, 2011

Reexamination Certificate for:
Patent No.: 7,714,152
Issued: May 11, 2010
Appl. No.: 11/847,422
Filed: Aug. 30, 2007

(51) Int. Cl.
*C07D 301/10* (2006.01)
*B01J 23/50* (2006.01)
*B01J 23/66* (2006.01)
*B01J 23/68* (2006.01)
*B01J 35/10* (2006.01)
*B01J 21/04* (2006.01)
*B01J 37/02* (2006.01)

(52) U.S. Cl.
CPC *B01J 23/50* (2013.01); *B01J 23/66* (2013.01); *B01J 23/687* (2013.01); *B01J 35/10* (2013.01); *C07D 301/10* (2013.01); *B01J 21/04* (2013.01); *B01J 35/1009* (2013.01); *B01J 35/1038* (2013.01); *B01J 35/1042* (2013.01); *B01J 35/1076* (2013.01); *B01J 35/108* (2013.01); *B01J 37/0213* (2013.01)
USPC ............ 549/536; 423/628; 502/348; 549/534

(58) Field of Classification Search
None
See application file for complete search history.

(56) References Cited

To view the complete listing of prior art documents cited during the proceeding for Reexamination Control Number 95/001,865, please refer to the USPTO's public Patent Application Information Retrieval (PAIR) system under the Display References tab.

*Primary Examiner* — Sharon Turner

(57) ABSTRACT

A carrier for a catalyst useful for the epoxidation of an olefin which comprises an inert, refractory solid carrier is provided. The carrier has no or little absolute volume from small pores, of less than 1 micrometer, and large pores, of above 5 micrometer. By "no or little absolute volume from small pores of less than 1 micron" it is meant that the pore volume of such pores is less than 0.20 ml/g. By "no or little absolute volume from large pores of above 5 micron" it is meant that the pore volume of such pores is less than 0.20 ml/g. The invention further provides a catalyst useful for the epoxidation of an olefin supported on such a carrier and a process for the oxidation of an olefin, especially ethylene, to an olefin oxide, especially ethylene oxide.

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-18 are cancelled.

* * * * *